United States Patent [19]

Ōmura et al.

[11] Patent Number: 4,533,547
[45] Date of Patent: Aug. 6, 1985

[54] ANTIVIRAL ANTIBIOTIC SUBSTANCE AM-2722 AND PROCESS FOR PRODUCTION THEREOF

[75] Inventors: Satoshi Ōmura; Akira Nakagawa; Hiroshi Hashimoto, all of Tokyo; Yasuhiko Kojima, Kanagawa; Yuzuru Iwai, Chiba; Ruiko Ōiwa, Kanagawa; Atsushi Hirano, Miyazaki, all of Japan

[73] Assignee: The Kitasato Institute, Japan

[21] Appl. No.: 262,242

[22] Filed: May 11, 1981

[30] Foreign Application Priority Data

May 10, 1980 [JP] Japan ................................ 55-61936

[51] Int. Cl.$^3$ ........................ H61K 35/74; C12P 1/06
[52] U.S. Cl. .................................... 424/122; 435/169
[58] Field of Search ...................... 424/122; 435/169

[56] References Cited

U.S. PATENT DOCUMENTS 4,038,384  7/1977  Berg et al. ........................... 424/122

Primary Examiner—Jerome D. Goldberg
Attorney, Agent, or Firm—Sughrue, Mion, Zinn, Macpeak and Seas

[57] ABSTRACT

A novel antiviral antibiotic AM-2722 is described represented by the molecular formula $C_{19}H_{26}NO_3Cl$, and having the following physicochemical properties:

(1) specific rotary power: $[\alpha]_D^{20} - 0.5$ (C—1, chloroform);
(2) the UV spectrum shown in FIG. 1; and
(3) the IR spectrum shown in FIG. 2.

Also described is a process for producing the antiviral antibiotic AM-2722, wherein a microorganism of Streptomyces which has the ability to produce the antibiotic AM-2722 is cultured aerobically in a nutrient medium and the antibiotic AM-2722 accumulated in the medium and the microorganism cells is recovered.

5 Claims, 3 Drawing Figures

ANTIVIRAL ANTIBIOTIC SUBSTANCE AM-2722 AND PROCESS FOR PRODUCTION THEREOF

FIELD OF THE INVENTION

The present invention relates to a novel antiviral antibiotic substance AM-2722 and a process for production thereof.

SUMMARY OF THE INVENTION

According to this invention, a novel antiviral antibiotic substance AM-2722 is provided, represented by the molecular formula $C_{19}H_{26}NO_3Cl$, and having the following physicochemical properties:

(1) specific rotary power: $[\alpha]_D^{20}-0.5$ (C=1, chloroform);
(2) the UV spectrum shown in FIG. 1; and
(3) the IR spectrum shown in FIG. 2.

A process is also provided according to the invention for producting the antiviral antibiotic substance AM-2722 wherein a microorganism of the genus Streptomyces which has the ability to produce the antiviral antibiotic substance AM-2722 is cultured aerobically in a nutrient medium and the antibiotic substance AM-2722 is accumulated in the medium or in the microorganism cells is recovered.

DETAILED DESCRIPTION OF THE INVENTION

It has been found that the strain AM-2722, of the genus Streptomyces has the ability to produce an antiviral antibiotic substance AM-2722 (referred to as hereafter "antibiotic AM-277" or simply "antibiotic"). The antibiotic AM-2722 has strong activity to inhibit the growth of various viruses of DNA and RNA types. The present invention is therefore based on the identification and isolation of the strain AM-2722, and the determination of useful physicochemical and biological properties of the isolated antibiotic AM-2722.

1. Physicochemical properties of the antibiotic AM-2722;

The antibiotic AM-2722 obtained by the present invention has the following physicochemical properties.

(1) Elemental analysis: 65.1% c, 7.1% H, 3.7% N, and 10.3% Cl.

Figure 3:
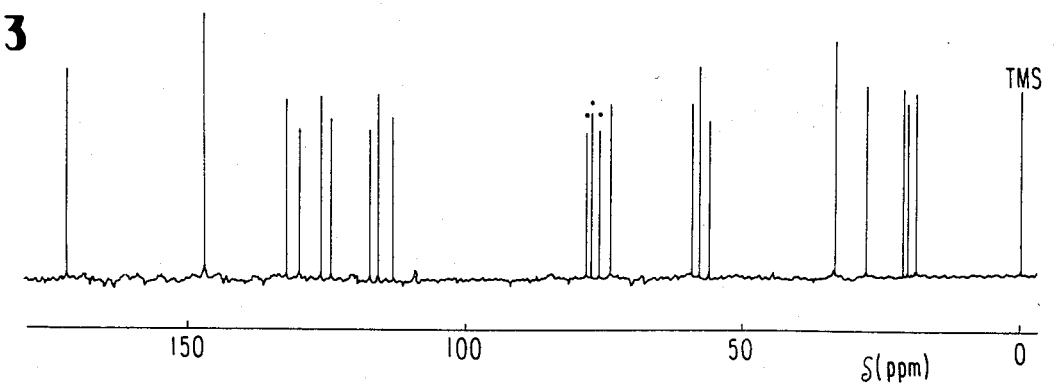
FIG. 3 is a C-13 NMR spectrum ($CDCl_3$).

(2) Molecular weight: 351 (M+ 351 according to high-resolution mass spectrometry; the elemental analysis and C-13 NMR spectrum (see FIG. 3) showed that the antibiotic has a molecular formula of $C_{19}H_{26}NO_3Cl$. The presence of one chlorine atom in the molecule was verified by elemental analysis, as well as by the Cl-based isotope peak in the mass spectrum.

(3) Melting point: 59° to 62° C.

(4) Specific rotary power: $[\alpha]_D^{20}-0.5$ (C=1, chloroform).

Figure 1:
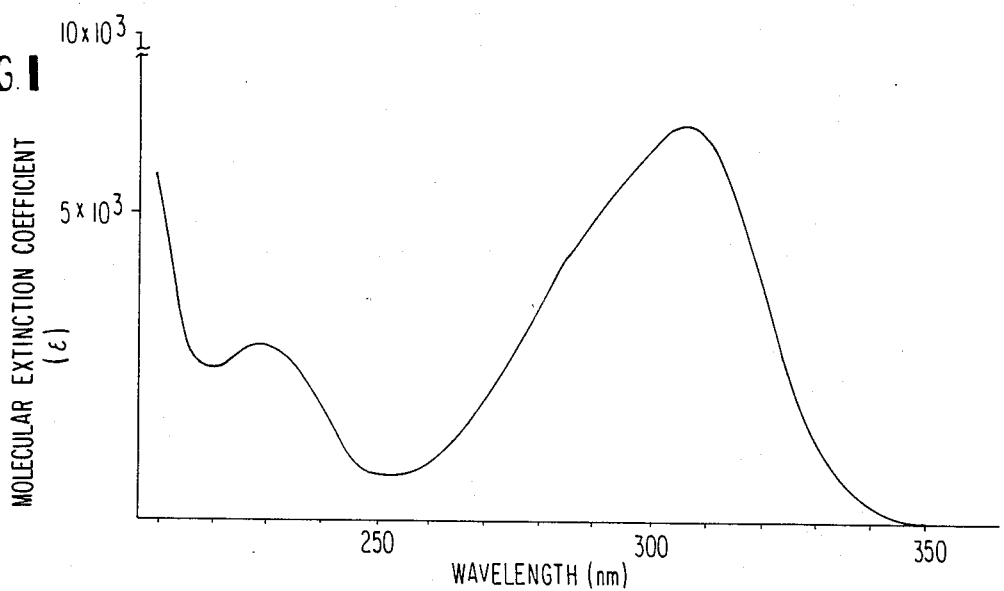
FIG. 1 is a UV spectrum of the antibiotic substance AM-2722.

(5) UV spectrum: Absorption maxima at 228 nm and 306 nm in ethanol, the molecular extinction coefficients being 3500 and 8100, respectively (see FIG. 1)

Figure 2:
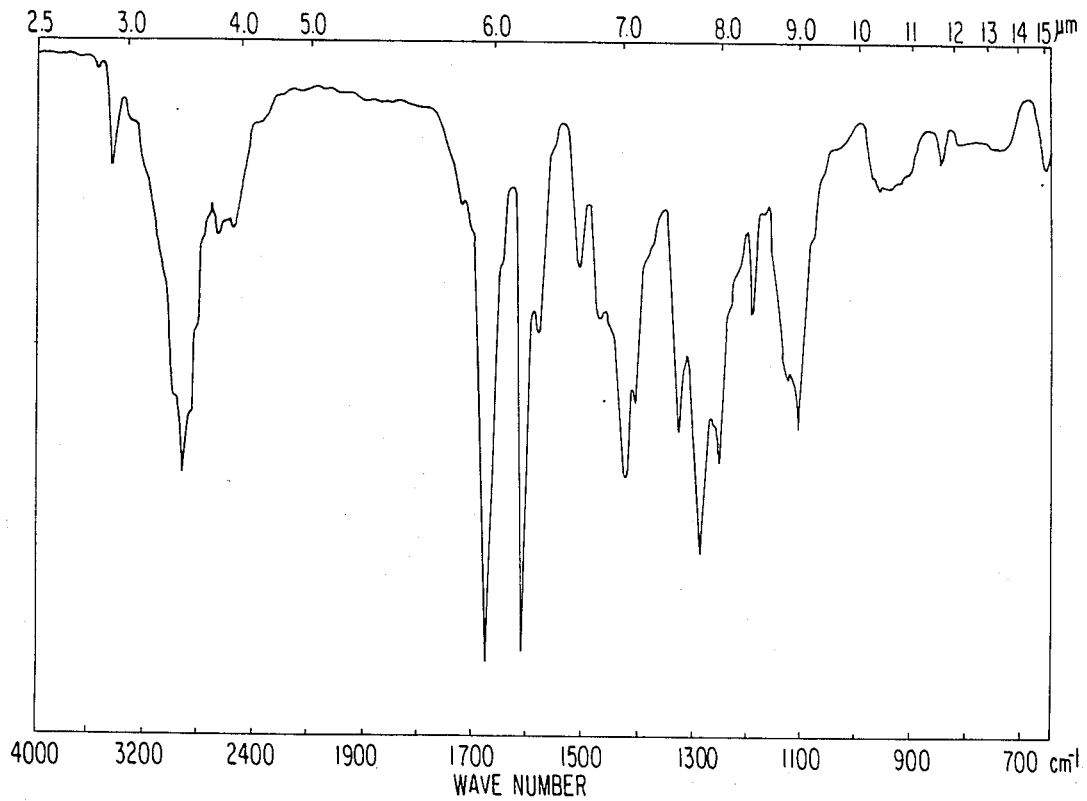
FIG. 2 is an IR spectrum of the antibiotic substance AM-2722 ($CCl_4$)

(6) IR spectrum: See FIG. 2 (solution method with carbon tetrachloride). Characteristic absorptions at 3,400–2,400 $cm^{-1}$ for a hydroxy group of a carboxylic acid, 1687 $cm^{-1}$ for a carbonyl group of an unsaturated carboxy acid, 3,440 $cm^{-1}$ for a tertiary amine, 1,100 $cm^{-1}$ for an ether bond, and 1,603 $cm^{-1}$ for a double bond.

(7) Solubility in solvents: Soluble in methanol, ethanol, acetone, chloroform, ethyl acetate, dimethyl sulfoxide and dimethylformamide, and insoluble in water, petroleum ether and n-hexane.

(8) Color reaction: Positive to hydroxamic acid-iron complex, Bromocresol Green, and iodine, and negative in Molisch reaction, Regal and ninhydrin reactions. Positive in Beilstein's flame reaction test (characteristic of chlorine atom).

(9) Weak acidic substance

(10) Thin-layer chromatography: Rf=0.47 (Silica gel GF 254 of Merck & Co., Ind., UV detection, benzene:acetone=2:1)

(11) C-13 NMR spectrum: See FIG. 3

Signals at $\delta=1,719$ ppm for one carbon atom of a carboxyl group, $\delta=147.2-113.5$ ppm for 8 carbon atoms of an aromatic ring and one double bond, signals at a high magnetic field for 3 carbon atoms of methyl group and 3 carbon atoms of methylene group, and other signals for 4 carbon atoms (total 19 carbon atoms).

As identified above, the antibiotic AM-2722 has little optical rotary power, has one chlorine atom in the molecule, has absorption maxima at 228 nm and 306 nm in the UV spectrum, and as described herein, has antiviral activity. In these respects, the antibiotic is novel and differs from known compounds. The antibiotic AM-2722 has the biological properties as described below.

2. Biological properties of the antibiotic AM-2722.

(1) Activity of inhibiting the growth of viruses: The activity of the antibiotic AM-2722 to inhibit the growth of viruses was assayed in terms of percent reduction (percent inhibition) of plaque formation. For the assay, primary chick embryonic cells (CE cells) were used. The following eight challenge viruses were used: for RNA type viruses, vesicular stomatitis virus (VSV), Sindbis virus (SbV), Western equine encephalitis virus (WEEV) and Newcastle disease virus (NDV), and for DNA type viruses, herpes simplex virus type 1 (HSV-1), herpes simplex virus type 2 (HSV-2), DIE strain of vaccinia virus (Vac-DIE), and IHD strain of vaccinia virus (Vac-IHD).

The activity of the antiviral antibiotic AM-2722 against these viruses was assayed by the following method: The antibiotic was successively diluted 10-fold (the initial concentration was 10 μg/ml) with an Eagle minimum essential culture medium supplemented with 2% calf serum (MEM/CS 2%), and the respective dilutions were inoculated with monolayers of CE cells, which were then cultured in a $CO_2$-filled incubator at 37° C. for 20 hours. The culture medium containing the antibiotic AM-2722 was removed and the CE cells was washed with phosphate-buffered saline. As a control, CE cells incubated only with the MEM/CS 2% were used. The CE cells washed with the buffer solution were inoculated with about 100 PFU (PFU: plaque forming unit) of each of the challenge viruses, left to stand at 37° C. for one hour for adsorbing the viruses onto the cells, and thereafter, the cells were transferred to a liquid mixture of 1% agar and MEM/CS 2% which were then solidified. The thus-fixed CE cells were held in a $CO_2$-filled incubator for two days for VSV, SbV and WEEV, for three days for HSV-1 and HSV-2, and for four days for Vac-DIE, Vac-IHD and NDV. The living cells were stained overlaying an agar containing 0.01% Neutral Red dye, and the number of plaques produced by the viruses was counted. The antiviral activity or percent plaque reduction (PR%) was calculated by subtracting from 100 the ratio, in percent, of the number of plaques for the cells treated with the antibiotic AM-2722 to that of plaques for the control cells. The minimum concentration of the antibiotic AM-2722 that achieved 50% PR was defined as the minimum inhibitory concentration (MIC) of the antibiotic. Table 1 shows the minimum inhibitory concentration against the respective viruses. As is clear from the table, VSV, SbV, WEEV, Vac-DIE, and Vac-IHD were inhibited by less than 0.01 $\mu$g/ml of the antibiotic, and NDV, HSV-1 and HSV-2 were inhibited by less than 0.1 $\mu$g/ml of the antibiotic. Thus, the antibiotic AM-2722 exhibited strong activity to inhibit various viruses of DNA and RNA types, and it can be considered a very useful substance that having a wider antiviral spectrum than previously reported antiviral substances such as Glyotoxin, Liphamycin, Arabinofuranocyladenine, and Distamycin. The antibiotic AM-2722 was not found to be toxic to the incubated CE cells at a concentration of less than 50 $\mu$g/ml.

TABLE 1

| Antiviral Activity-Plaque Reduction Test | |
|---|---|
| Virus | MIC - $\mu$g/ml |
| [RNA virus] | |
| VSV | 0.008 |
| SbV | 0.006 |
| WEE | 0.003 |
| NDV | 0.04 |
| [DNA virus] | |
| Vac-DIE | 0.005 |
| Vac-IHD | 0.004 |
| HSV-1 | 0.03 |
| HSV-2 | 0.02 |

(2) Activity of inhibiting the growth of fungi and yeasts: Table 2 shows the anti-fungal and anti-yeast spectrum of the antibiotic AM-2722 obtained by agar dilution method. As Table 2 shows, the minimum inhibitory concentration of the antibiotic against various fungi and yeasts was in the range of from 25 to 50 $\mu$g/ml.

TABLE 2

| Spectrum of Anti-fungal and Anti-yeast Activity of Antibiotic AM-2722 | |
|---|---|
| Microorganism | MIC $\mu$g/ml* |
| Candida albicans | 50 |
| Sacchaaromyces sake | 25 |
| Piricularia oryzae | 25 |
| Trichophyton interdigitale | 25 |
| Aspergillus niger | 12.5 |
| Alternaria kikuchiana | 25 |
| Mucor racemosus | 25 |

*MIC determined after incubation on potato-glucose agar medium at 27° C. for 2~4 days.

(3) Toxicity

The LD$_{50}$ of the antibiotic AM-2722 in mice by intraperitoneal administration was 5 mg/kg.

The antibiotic AM-2722 can be produced by Strain AM-2722 of Streptomyces sp. which has newly been isolated from a putrefied pumpkin.

(1) Morphological properties

The vegetative hyphae of the microorganism grew well both on a natural medium and on a synthetic medium, and they usually had no septal wall. The growth of aerial mycellia was abundant on a yeast-malt agar medium, starch-inorganic salt agar medium, glucose-asparagine agar medium, and tyrosine agar medium, and small or absent on a glycerine-calcium malate agar medium, glucose-nitrate agar medium, and peptone-yeast iron agar medium. The aerial mycellia were white to gray and most of them were velvety. Under microscope straight or looped sporophores forming chains of more than ten spores were observed. The spores were almost oval measuring 0.4~0.5×1.0~1.1 $\mu$ and had a smooth surface. No sclerotium, sporangium, or flagellated swarm cells was found.

(2) Growth on various media

The strain AM-2722 was incubated on known media according to the combination of the method of E. B. Shirling et al. (Int. J. Syst. Bacteriol, 16, p. 313, 1966) and the known technique of experiment. The results are set forth in Table 3. For describing the color formations, the Color Harmony Manual, 4th ed., 1958, published by the Container Corporation of America, Chicago, U.S.A. was used as a reference. The color designation consists of a color chip name followed by a parenthesized code number. Unless otherwise noted, all data in the table are based on a 2-week incubation at 27° C.

TABLE 3

| Cultural characteristics of strain AM-2722 | |
|---|---|
| Glucose-nitrate agar | G: thin, pearl (3ba) |
| | R: pearl (3ba) |
| | AM: poor, velvety, natural (3dc) |
| | SP: none |
| Sucrose-nitrate agar | G: moderate, colorless |
| | R: colorless |
| | AM: moderate, velvety, ivory tint (2cb) |
| | SP: none |
| Glycerol-calcium malate agar | G: moderate, flat and penetrate, colorless |
| | R: colorless |
| | AM: poor, velvety, white-gray (a–g) |
| | SP: none |
| Glucose-asparagine agar | G: good, slightly raised, bamboo (2gc) |
| | R: bamboo (2gc) |
| | AM: abundant, velvety, ivory tint (2cb) |
| | SP: none |
| Glycerol-asparagine agar (ISP) | G: good, slightly raised, yellow tint (1ba) |
| | R: covert brown (2nl) |
| | AM: abundant, powdery, gray (d) |
| | SP: none |
| Inorganic salts-starch agar (ISP)* | G: good, slightly rased, colorless |
| | R: colorless |
| | AM: abundant, velvety, gray (d) |
| | SP: none |
| Tyrosine agar (ISP)* | G: good, penetrate, pearl pink (3ca) |
| | R: gray (f) |
| | AM: abundant, velvety, gray (d) |
| | SP: light brownish gray (5cb) |
| Yeast extract-malt extract agar (ISP)* | G: good, wrinkled, raised, light ivory (2ca) |
| | R: light ivory-covert brown (2ca - 2li) |
| | AM: abundant, water drop, velvety, gray (b–d) |
| | SP: none |
| Oatmeal agar (ISP)* | G: moderate, flat, colorless |
| | R: colorless |
| | AM: moderate, velvety, gray (h) |
| | SP: none |
| Peptone-yeast extract iron agar (ISP)* | G: thin, bamboo (2gc) |
| | R: bamboo (2gc) |
| | AM: none |
| | SP: none |
| Glucose-peptone agar | G: moderate, raised, cream (1½ ca) |
| | R: cream (1½ ca) |
| | AM: moderate, velvety, white (a) |

TABLE 3-continued

| Cultural characteristics of strain AM-2722 | |
|---|---|
| Nutrient agar | SP: none |
| | G: good, penetrate, light wheat (2 ea) |
| | R: light wheat (2 ea) |
| | AM: moderate, velvety, white (a) |
| | SP: none |

Abbreviations used in Table 3: G, growth; R, reverse; AM, aerial mycelium; Sp, soluble pigment.
*,Medium employed by The International Streptomyces Project.

(3) Physiological properties

| Melanin formation | − |
|---|---|
| Tyrosinase reaction | − |
| H$_2$S production | − |
| Nitrate reduction | + |
| Liquefaction of gelatin | − |
| Hydrolysis of starch | + |
| Coagulation of milk | − |
| Peptonization of milk | + |
| Cellulolytic activity | − |
| Temp. range of growth | 22° C.–34° C. |

(4) Utilization of carbon sources by strain AM-2722

Positive: D-glucose, L-arabinose, D-xylose, rahmnose

Doubtful: sucrose, D-fructose, D-mannitol

Negative: i-inositol, raffinose (5) Composition of cell wall

LL-type diaminopimelic acid present, arabinose or galactose not found.

The mycological observations of the strain AM-2722 described above can be summarized as follows: The cell wall of the strain included LL-diaminopimelic acid. The strain had straight or looped sporophores and smooth-surfaced spores. The vegetative mycellia were yellow to pale brown, and their color was independent of pH. The aerial mycellia were white to gray. No soluble pigment or melamine pigment was produced.

From these results, it was concluded that the strain AM-2722 belongs to Streptomyces, as well as to the white or gray series according to classification by Pridham and Tresner in *Bergey's Manual of Determinative Bacteriology*, 8th, Ed., pp. 748–829, 1974). The strain has been deposited with the Fermentation Research Institute, Agency of Industrial Science and Technology, Japan, as Streptomyces sp. AM-2722 under FERM P No. 5419 deposited Feb. 26, 1980.

The microorganism that can be used in this invention includes not only Streptomyces sp. AM-2722 and mutants thereof, but also any of the microorganisms of Streptomyces that have the ability to produce the antibiotic AM-2722. Any of the media that contains a carbon source, nitrogen source, minerals and suitable amounts of other optional nutrients can be used in this invention. Examples of the carbon source include various carbohydrates such as glucose, glycerine, fructose, maltose, dextrin, lactose, mannitol, galactose, starch and liquid hydrolyzates thereof. Examples of the nitrogen source include ammonia and various inorganic and organic ammonium salts such as ammonium chloride, ammonium phosphate, ammonium sulfate and ammonium nitrate, as well as urea, peptone, meat extract, dried yeast, yeast extract and soybean flour. These nitrogen sources may be used alone or in combination. Examples of the mineral are various phosphates, magnesium sulfate and trace amounts of heavy metal salts. A medium containing natural products does not necessarily have to contain an added mineral source.

The strain AM-2722 can be fermented under aerobic conditions by shake cultivation or submerged cultivation under aereration and agitation. The cultivation temperature is generally in the range of from 15° C. to 40° C. The cultivation period is generally from 1 to 4 days, and in this period, the antibiotic AM-2722 is produced in the broth and the microorganism cells. After the cultivation, the broth and microorganism cells are subjected to the isolation of antibiotic AM-2722: the culture is separated into the microorganism cells and the filtrate; the cells are extracted with an organic solvent such as acetone or methanol whereas the filtrate is extracted with ethyl acetate, butyl acetate, benzene, chloroform or other organic solvents that are not miscible with water and which dissolve the antibiotic AM-2722; the extracts are combined and concentrated to dryness under vacuum. The antibiotic AM-2722 is recovered from the crude extract by a known method that is commonly employed in the purification of fat-soluble substances, for example, by adsorbing on an adsorbent such as silica gel and alumina using an adsorption chromatography and elute with an organic solvent.

This invention is now described in greater detail by reference to the following examples which are given here for illustrative purposes only, and are not intended to limit the scope of the invention.

EXAMPLE 1

A germination medium was inoculated with a loopful of a slant culture of Streptomyces sp. AM-2722 (FERM P No. 5419), and incubated at 27° C. for 2 days. A 1% inoculum from the germination stage was transferred to a 50-liter jar fermentor containing 30 liters of a medium, and cultured under aeration and agitation at 27° C. for 2 days. Both cultures for germination and fermentation contained 2.0% glucose, 0.5% peptone, 0.3% dried yeast, 0.5% sodium chloride and 0.3% calcium carbonate, and they were adjusted to a pH of 7.0 and sterilized at 120° C. for 15 minutes. The culture broth (28 liters) was separated by centrifuge into a filtrate (21 liters) and microorganism cells. The filtrate was adjusted to a pH of 3 with concentrated hydrochloric acid, and ethyl acetate (10 liters) was added thereto, and stirred for about 30 minutes, followed by centrifugation. The thus separated ethyl acetate layer was concentrated under vacuum to obtain 12 g of a red brown oily product. The cells were extracted with methanol (1.8 liters), and the extract was concentrated under vacuum. Ethyl acetate (0.5 liter) was added to the concentrate (0.5 liter) to extract the antibiotic AM-2722. The ethyl acetate layer was concentrated under vacuum to give a red brown oily product (4.5 g). The crude products from the filtrate and cells were combined, and dissolved in benzene (500 ml) and the impurities insoluble in benzene were removed by filtration. The benzene solution was concentrated under vacuum to dryness, and the concentrate was dissolved in chloroform (ca. 100 ml). The solution was passed through a column of silica gel (Kiesel gel 60 of Merck & Co., Inc., 600 g) which was eluted with 3 liters of a mixture of chloroform/methanol/acetic acid (70:1:0.025). The resulting fractions each measuring 20-ml were subjected to thin-layer chromatography separations (Kiesel gel GF 254 of Merck & Co., Inc., 0.25 nm, developer=benzene/acetone (2:1)), and fractions 60 to 120 containing a substance having an Rf of 0.47 which turned purple upon exposure to a UV lamp (product of MANASUL Chemical Industries Co., Ltd., 253.7 nm, 365 nm) were combined and concentrated to dryness under vacuum to provide a brown oily product (1.5 g). The product was dissolved in benzene and subjected to column chromatography using a silica gel (Kiesel gel 60 of Merck & Co., Ind., 40 g) which was eluted with a solvent (benzene:acetone=20:1). Resulting 5-ml fractions were subjected to thin-layer chromatography under the same conditions as used above, and fractions 16 to 32 composed of a single substance that had an Rf of 0.47 were combined and concentrated to dryness under vacuum to provide a white powder of the antibiotic AM-2722 (280 g).

EXAMPLE 2

By repeating the procedure of Example 1, a culture broth (28 liters) was obtained. It was adjusted to a pH of 3 with concentrated hydrochloric acid and separated by centrifuge into a filtrate and the microorganism cells. The filtrate (21 liters) was extracted with ethyl acetate (10 liters) and the microorganism cells with methanol (1.8 liters) to give red brown oily products in a manner similar to those in Example 1, which were combined and dissolved in chloroform (300 ml) and the impurities insoluble in chloroform were removed. The chloroform solution was concentrated to dryness, and the resulting oily product (15.5 g) was purified by preparative high-speed chromatography (System 500 of Waters Ltd.) under the following conditions: a solution of the oily product in a mixture (20 ml) of chloroform and methanol (30:1) and passed through a column packed with 300 g of a silica gel (PLEP-pack 500) which was eluted with solvent (2 liters) made of chloroform and methanol (30:1) at 30 atm. and a rate of 250 ml/min. The resulting 250 ml fractions were treated subsequently in the same manner as in Example 1, and fractions 3 to 5 composed of the single desired substance were combined and concentrated to dryness under vacuum to provide a white powder of the antibiotic AM-2722 (200 mg).

While the invention has been described in detail and with reference to specific embodiments thereof, it will be apparent to one skilled in the art that various changes and modifications can be made therein without departing from the spirit and scope thereof.

What is claimed is:

1. An antiviral antibiotic AM-2722 represented by the molecular formula $C_{19}H_{26}NO_3Cl$, and having the following physicochemical properties:
   (1) specific rotary power $[\alpha]_D^{20} - 0.5$ (C=1, chloroform);
   (2) the UV spectrum shown in FIG. 1; and
   (3) the IR spectrum shown in FIG. 2.

2. A process for producing an antiviral antibiotic AM-2722 represented by molecular formula $C_{19}H_{26}NO_3Cl$ and having the following physiochemical properties:
   (1) specific rotary power $[\alpha]_D^{20} - 0.5$ (C=1, chloroform);
   (2) the UV spectrum shown in FIG. 1; and
   (3) the IR spectrum shown in FIG. 2,
wherein a microorganism of the genus Streptomyces which has the ability to produce the antiviral antibiotic AM-2722 is cultured aerobically on a nutrient medium and the antibiotic AM-2722 accumulated in the medium until a substantial antibiotic activity is imparted to said medium and the microorganism cells are then recovered, wherein said microorganism is Streptomyces sp. AM-2722 having the FERM designation FERM P No. 5419 and wherein the cultivation temperature is in the range of 15° C. to 40° C.

3. A process as in claim 2 wherein the antibiotic AM-2722 is recovered by a solvent extraction technique.

4. A process as in claim 2 wherein the cultivation period is from 1 to 4 days.

5. A process for producing the antiviral antibiotic AM-2722 as in claim 2, wherein said nutrient medium contains a carbon source, a nitrogen source, and minerals.

* * * * *